United States Patent
McNair

(10) Patent No.: US 10,390,765 B1
(45) Date of Patent: Aug. 27, 2019

(54) DECISION SUPPORT SYSTEM FOR ANTICIPATING A MYOCARDIAL ISCHEMIC EVENT

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 368 days.

(21) Appl. No.: 15/395,696

(22) Filed: Dec. 30, 2016

Related U.S. Application Data

(60) Provisional application No. 62/273,948, filed on Dec. 31, 2015.

(51) Int. Cl.

| | |
|---|---|
| *A61B 5/02* | (2006.01) |
| *A61B 5/00* | (2006.01) |
| *A61B 5/0205* | (2006.01) |
| *A61B 5/145* | (2006.01) |
| *A61B 5/024* | (2006.01) |
| *A61B 5/021* | (2006.01) |

(52) U.S. Cl.
CPC .......... *A61B 5/7278* (2013.01); *A61B 5/0015* (2013.01); *A61B 5/0205* (2013.01); *A61B 5/14542* (2013.01); *A61B 5/7275* (2013.01); *A61B 5/021* (2013.01); *A61B 5/024* (2013.01)

(58) Field of Classification Search
None
See application file for complete search history.

(56) References Cited

U.S. PATENT DOCUMENTS

| | | | | |
|---|---|---|---|---|
| 2009/0292180 A1* | 11/2009 | Mirow | ................... | G16H 10/20 600/301 |
| 2011/0190650 A1* | 8/2011 | McNair | .................... | A61B 5/00 600/518 |
| 2014/0121550 A1* | 5/2014 | McNair | .................... | A61B 5/00 600/509 |
| 2014/0134654 A1* | 5/2014 | Rudel | .................... | G01N 33/92 435/11 |
| 2014/0135637 A1* | 5/2014 | Bardy | .................. | A61B 5/0006 600/509 |
| 2014/0135859 A1* | 5/2014 | Bardy | .................. | A61B 5/0006 607/3 |

* cited by examiner

*Primary Examiner* — Ankit D Tejani
(74) *Attorney, Agent, or Firm* — Shook, Hardy & Bacon L.L.P.

(57) ABSTRACT

A catastrophe-theoretic approach is provided for predicting an occurrence of an ischemic myocardial event (e.g., acute myocardial infarction) for a human patient based on a time series of monitored vital signs values measured from a patient, and in some instances, for providing advanced notice to clinicians or caregivers when such an ischemic event is forecasted or modifying treatment for the patient, according to the predicted likelihood. In particular, an ischemic heart disease management system is provided for determining a likelihood of near-term future significant myocardial ischemia in persons with coronary artery disease. Embodiments of the disclosure described herein may provide a forecasted risk for future significant myocardial ischemia within a time horizon comprising a future time interval. In one embodiment, the future time interval is from 30 min to approximately 4 hours into the future, and may be dependent on the frequency of vital signs measurements.

20 Claims, 13 Drawing Sheets

CUSP CATASTROPHE AND ISCHEMIA ALARM
SIGNAL PLOTS – EXAMPLE "G" (CONTINUED)

```
###############################################################################

#  Catastrophe Modeling of HR Data For AMI Prediction

######################################################################### library(cusp)

load data
mon1 <- read.csv(file="c:/0_cerdsm/IP/AMI_HRV/mon1.csv", header=TRUE,
         colClasses=rep("numeric",4))
hr, sbp, rpp, spo2 inits
N <- length(mon1[,1]) - 200
AIC.ts <- rep(0, N)
perf <- rep(" ", N)
seg <- matrix(rep(0, N), ncol=4)
colnames(seg) <- c("hr","sbp","rpp","spo2")
alarm.isch <- rep(0, N)
ewma <- 0 calculate time series of AIC differences between cusp model and linear model
for (i in 350:N){
  seg <- mon1[i:200+i,]
  # center and standardize to SD=1
  seg[,1] <- scale(seg[,1], center=TRUE)
  seg[,2] <- scale(seg[,2], center=TRUE)
  seg[,3] <- scale(seg[,3], center=TRUE)
  seg[,4] <- -scale(seg[,4], center=TRUE) # invert SpO2 so that desaturation is high
  # calculate cusp and linear models
  set.seed(1239)
  fit <- cusp(y ~ rpp, alpha ~ hr + sbp, beta ~ hr + spo2, data=seg)
  # log Hessian and convergence properties
  perf[i] <- paste0('N: ', i, ' OK: ', fit$OK, ' conv:', fit$converged)
  # compare linear vs. cusp models AIC values
  fit.res <- summary(fit)
  AIC.ts[i] <- abs(fit.res$r2lin.aicc/fit.res$r2cusp.aicc[1])
  # calculate EWMA of log signal
  if(i > 2) ewma <- 0.6*log(AIC.ts[i] + 1) + 0.3*log(AIC.ts[i-1] + 1) + 0.1*log(AIC.ts[i-2] + 1)
  if(ewma > 5) alarm.isch[i] <- 1
} load dataset2
mon2 <- read.csv(file="c:/0_cerdsm/IP/AMI_HRV/mon2.csv", header=TRUE,
         colClasses=rep("numeric",4))
hr, sbp, rpp, spo2 inits
N <- length(mon2[,1]) - 200
AIC.ts <- rep(0, N)
perf <- rep(" ", N)
seg <- matrix(rep(0, N), ncol=4)
colnames(seg) <- c("hr","sbp","rpp","spo2")
alarm.isch <- rep(0, N)
ewma <- 0
```

CONTINUES IN FIG. 7B

CONTINUES FROM FIG. 7A

.
.
.

```
# calculate time series of AIC differences between cusp model and linear model
for (i in 350:N){
  seg <- mon2[i:200+i,]
  # center and standardize to SD=1
  seg[,1] <- scale(seg[,1], center=TRUE)
  seg[,2] <- scale(seg[,2], center=TRUE)
  seg[,3] <- scale(seg[,3], center=TRUE)
  seg[,4] <- -scale(seg[,4], center=TRUE) # invert SpO2 so that desaturation is high
  # calculate cusp and linear models
  set.seed(1239)
  fit <- cusp(y ~ rpp, alpha ~ hr + sbp, beta ~ hr + spo2, data=seg)
  # log Hessian and convergence properties
  perf[i] <- paste0('N: ', i, ' OK: ', fit$OK, ' conv:', fit$converged)
  # compare linear vs. cusp models AIC values
  fit.res <- summary(fit)
  AIC.ts[i] <- abs(fit.res$r2lin.aicc/fit.res$r2cusp.aicc[1])
  # calculate EWMA of log signal
  if(i > 2) ewma <- 0.6*log(AIC.ts[i] + 1) + 0.3*log(AIC.ts[i-1] + 1) + 0.1*log(AIC.ts[i-2] + 1)
  if(ewma > 5) alarm.isch[i] <- 1
} plot signal
plot(log(AIC.ts[350:800] + 1), ty="l", col="red", lwd=2)
plot(alarm.isch[350:800], ty="l", col="red", lwd=2)

# plot example positive-control segment (proven antecedent ischemic episode,
followed by elevated cTnI levels and ECG changes)
  seg <- mon[351:850,]
  # center and standardize to SD=1
  seg[,1] <- scale(seg[,1], center=TRUE)
  seg[,2] <- scale(seg[,2], center=TRUE)
  seg[,3] <- scale(seg[,3], center=TRUE)
  seg[,4] <- -scale(seg[,4], center=TRUE) # invert SpO2 so that desaturation is high
  # calculate cusp and linear models
  set.seed(1222)
  fit <- cusp(y ~ rpp, alpha ~ hr + sbp, beta ~ hr + spo2, data=seg,
control=list(epsilon=1e-4, maxit=150, trace=FALSE), logist=TRUE)
  summary(fit, logist=TRUE)
# fit <- cusp(y ~ rpp, alpha ~ hr + sbp, beta ~ hr + spo2, data=seg, start=rnorm(fit$par))
  cusp3d(fit, B=4.5, n.surf=50, theta=150, phi=40)
  plot(fit)
```

*FIG. 7B*

DECISION SUPPORT SYSTEM FOR ANTICIPATING A MYOCARDIAL ISCHEMIC EVENT

CROSS-REFERENCE TO RELATED APPLICATIONS

This application claims priority to U.S. Provisional Application No. 62/273,948, entitled "Predicting Myocardial Ischemic Events," filed Dec. 31, 2015. The aforementioned application is hereby incorporated by reference herein.

BACKGROUND

Ischemic heart disease is a condition caused by coronary arteries that are narrowed. Narrowing of the lumen of coronary arteries means less blood and oxygen reaches the heart muscle ('myocardium'). When more oxygen is needed, such as while exercising, sometimes the heart cannot meet the body's metabolic demand. An insufficiency of oxygen caused by ischemic heart disease can produce chest pain, known as angina pectoris, and ischemic myocardial events such as acute coronary syndrome (ACS) or acute myocardial infarction ('heart attack'). According to data from NHANES 2007 to 2010 (U.S. National Heart Lung and Blood Institute NHLBI tabulation), the overall prevalence for the ischemic cardiac event resulting in death of myocardial muscle tissue, termed acute myocardial infarction or AMI, is 2.9% in U.S. adults greater than 20 years of age. AMI prevalence is 4.2% for men and 1.7% for women. Patients who have experienced one or more ischemic myocardial events in the past are at the greatest risk of incurring additional ischemic myocardial events subsequently. While there have been attempts to provide a technological solution through decision support systems, these systems have significant drawbacks and cannot provide the reliability and accuracy of the systems and processes proposed in the present disclosure.

SUMMARY

Systems, methods and computer-readable media are provided for predicting an occurrence of ischemic myocardial events based on a time series of monitored vital signs values measured from a patient, and in some instances, for providing advanced notice to clinicians or caregivers when such an ischemic event is forecasted or modifying treatment for the patient, according to the predicted likelihood. In particular, an ischemic heart disease management system is provided for determining a likelihood of near-term future significant myocardial ischemia in persons with coronary artery disease. Embodiments of the disclosure described herein may provide a forecasted risk for future significant myocardial ischemia within a time horizon comprising a future time interval. In one embodiment, the future time interval is from 30 min to approximately 4 hours into the future, and may be dependent on the frequency of vital signs measurements.

A catastrophe-theoretic approach is provided, for determining the predicted ischemic myocardial event, which does not require patient measurements to be acquired on a regular or periodic basis. In one aspect, a vital signs time series is determined for a candidate patient. From the time series, a linear model and cusp catastrophe model is calculated, and goodness-of-fit measures are determined. A likelihood of future myocardial ischemia occurrence is then determined within a future time interval, based on whether threshold for the smoothed cusp model is transgressed or, alternately, based on whether a threshold for the ratio of linear-to-cusp model values is exceeded. Based on the determined likelihood, a set of one or more actions may be initiated. One action comprises generating a notification that may be emitted or otherwise communicated to a provider clinician(s) responsible for the care of the patient. Another action that may be initiated, based on the determined likelihood, comprises a recommendation for modifying a care plan or treatment procedure associated with the patient. Yet another action that may be initiated, based on the determined likelihood, comprises automatically modifying computer code executed in a healthcare software program for treating the patient, thereby transforming the program at runtime.

Accordingly, one aim of embodiments of this disclosure is to improve upon conventional industry practice. The improvement relates to deriving accurate predictive capabilities from moderate-frequency, potentially-aperiodic time series such as accrue with continuous monitoring in acute care environments. In this way, embodiments described herein overcome deficiencies in the prior art as they are robust (a) against temporary sensor artifacts or intermittent gaps or failures to perform periodic measurements, (b) against delays in uploading or synchronizing newly acquired patient physiological values with historical vital signs time series measured in the patient, and (c) against non-stationarity in the time series, such as may arise during periods when the patient's health deviates from predominant patterns, due to health conditions or physiologic phenomena that alter autonomic sympathetic-parasympathetic tone and neuroendocrine regulation, such as when the patient has systemic inflammatory response syndrome (SIRS) or sepsis. Moreover, forecasting one or more event occurrences within a near-term future interval, such as a 4-hour time horizon, provides a valuable benefit. Such a timeframe is long enough that an actionable occurrence is quite likely for many patients, but not so long that the risk of the event is omnipresent such that alert signals become annoying or a cause of "alert fatigue".

BRIEF DESCRIPTION OF THE DRAWINGS

The present invention is described in detail below with reference to the attached drawing figures, wherein:

FIGS. 7A and 7B depict an example embodiment of a computer program routine for predicting an occurrence of an ischemic myocardial event for a human patient within a future time interval, in accordance with an embodiment of the disclosure.

DETAILED DESCRIPTION

Figure 1A:
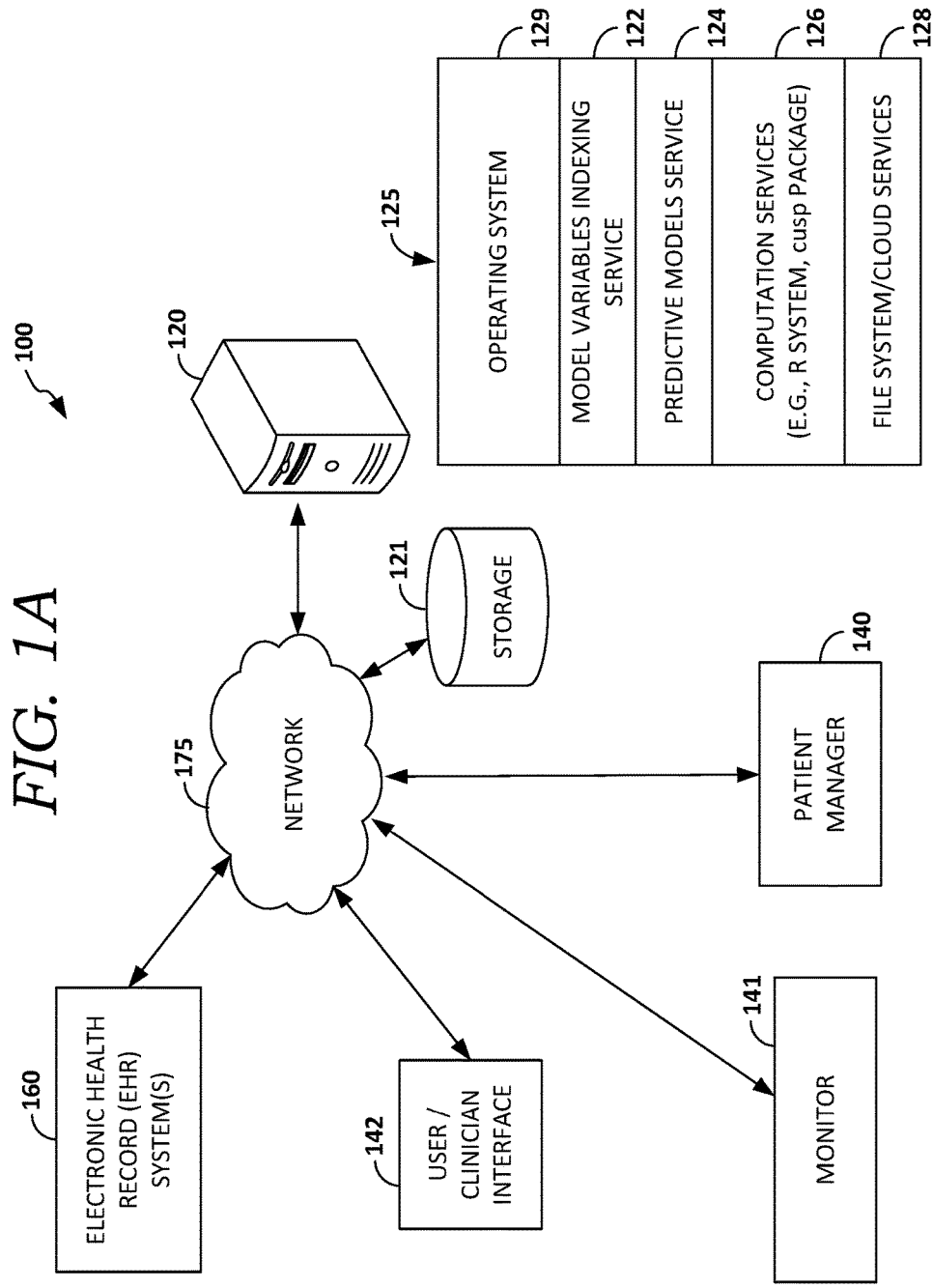
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, at a high level, this disclosure describes, among other things, methods and systems, for predicting an occurrence of a ischemic myocardial event based on a time series of monitored vital signs values measured from a patient, and in some instances, for providing advanced notice to clinicians or caregivers when such an ischemic event is forecasted or modifying treatment for the patient, according to the predicted likelihood. In particular, ischemic heart disease management systems and methods are provided for determining a likelihood of near-term future significant myocardial ischemia in persons with coronary artery disease. Embodiments of the disclosure described herein may provide a forecasted risk for future significant myocardial ischemia within a time horizon comprising a future time interval. In one embodiment, the future time interval is from 30 min to approximately 4 hours into the future, and may be dependent on the frequency of vital signs measurements.

In some embodiments, a catastrophe-theoretic approach is provided for determining the predicted ischemic myocardial event, which does not require patient measurements to be acquired on a regular or periodic basis. In one aspect, a vital signs time series is determined for a candidate patient. In one embodiment, the time series comprises at least 100 samples, and in one embodiment, the values of the vital-signs variables may be standardized and/or centered. From the time series, a linear model and cusp catastrophe model is calculated, and goodness-of-fit measures are determined. In one embodiment, the goodness-of-fit measure comprises the Akaike Information Criterion (AIC). Further, in one embodiment, the time series may be smoothed such as by applying using Exponentially-Weighted Moving Average (EWMA). A likelihood of future myocardial ischemia occurrence is then determined within a future time interval, based on whether threshold for the smoothed cusp model is transgressed or, alternately, based on whether a threshold for the ratio of linear-to-cusp model values is exceeded. In one embodiment, the future time interval and/or thresholds are pre-determined; for example, the future time interval may be within 4 hours, and the threshold determined based in part on a particular patient context, such as the patient's condition, resources available for caring for the patient, and/or the intensity of care being received by the patient. The determined likelihood may be stored in an EHR associated with the patient, where it may be used for comparison in a subsequent prediction of a myocardial ischemic event.

Based on the determined likelihood, a set of one or more actions may be initiated. One action comprises generating a notification that may be emitted or otherwise communicated to a provider clinician(s) responsible for the care of the patient. In an embodiment, the action comprises generating and emitting or communicating the notification, which may be emitted/communicated via a bedside alarm, user/clinician interface (such as interface 142 described in FIG. 1A), or may be communicated to a smartphone or personal computing device of a caregiver, thereby alerting them of an impending deterioration of the patient's condition. In one embodiment, the notification comprises an event signal and includes the likelihood of future myocardial ischemia occurrence.

Another action that may be initiated, based on the determined likelihood, comprises a recommendation for modifying a care plan or treatment procedure associated with the patient; for example, a recommendation may comprise increasing patient monitoring or level of care, operating on the patient, or administering a therapeutic intervention, such as a medication or procedure. The recommendation may be provided in conjunction with a notification of the likelihood or a future myocardial ischemia occurrence, and/or may be provided via a user/clinician interface, such as interface 142, described in connection with FIG. 1A.

Yet another action that may be initiated, based on the determined likelihood, comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the determined likelihood of future myocardial ischemia occurrence. In one instance, the modification comprises changing the executed computer instructions corresponding to monitoring the patient's condition, such as increasing the frequency of obtaining physiological measurements of the patient, or increasing sensitivity of monitoring physiological changes in a patient.

Yet another action that may be initiated, based on the determined likelihood, comprises scheduling healthcare resources for the patient. For example in one embodiment, an operating room (OR) resource may be automatically reserved for the patient, OR staff may be notified and/or automatically scheduled, and transportation/support staff or resources for getting the patient to the OR may be called. In one embodiment, this action comprises modifying or updating a resource/scheduling electronic record in a resource/scheduling system, such as operated as part of a hospital system. In one embodiment, the action comprises, upon a sufficient determined likelihood of a future myocardial ischemia occurrence (wherein significance may be determined using a threshold, as described in method 200 of FIG. 2), initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources.

As described previously, one aim of embodiments of this disclosure relates to deriving accurate predictive capabilities from moderate-frequency, potentially-aperiodic time series such as accrue with continuous monitoring in acute care environments. Existing approaches that utilize models derived from time series of measurements generally impose a variety of assumptions regarding the linear properties and stationarity (constancy over time) of the physiologic processes that give rise to the vital signs or hemodynamics time series—assumptions which may not be met for all patients, or may not be met at various times in any particular patient. As a result, model misspecification of non-ignorable effects frequently degrades prediction accuracy, which creates significant drawbacks in the current technology. In view of this, a non-parametric system and method that does not require a priori specification of model structure, such as described herein, is preferable, in particular where such embodiments comprise a non-parametric system or method that is robust against time series non-stationarity and aperiodicity of vital signs measurements, as further described herein.

Accordingly, embodiment of the present disclosure determine a qualitative model predicting near-term ischemic myocardial events based on catastrophe-theoretic modeling of vital signs time series. In this way, embodiments described herein are robust (a) against temporary sensor artifacts or intermittent gaps or failures to perform periodic measurements, (b) against delays in uploading or synchronizing newly acquired patient physiological values with historical vital signs time series measured in the patient, and (c) against non-stationarity in the time series, such as may arise during periods when the patient's health deviates from predominant patterns, due to health conditions or physiologic phenomena that alter autonomic sympathetic-parasympathetic tone and neuroendocrine regulation, such as when the patient has systemic inflammatory response syndrome (SIRS) or sepsis.

Patients who enter acute care with a new ischemic myocardial event are often placed in a Coronary Care Unit (CCU), a type of critical care venue, and are connected to sensor equipment for continuous monitoring of vital signs and electrocardiogram (ECG). However, patients may also enter acute care for some other non-cardiac reason but have a history of previous ischemic myocardial event(s) in the past. Such patients are often placed in routine medical-surgical beds, where nurses and other clinicians may not have such extensive knowledge and experience regarding hemodynamics and cardiac observations, and where continuous monitoring equipment may or may not be attached to the patient.

The development of methods for continuous non-invasive recording of vital signs (which may be embodied as one or more patient monitors, such as monitor 141 described in FIG. 1A) has had a growing impact on the evolution of acute care medicine in such settings outside of critical care units. These devices and methods afford substantial advances in screening hemodynamic status during routine care, and management of intermediate-risk patients who are not sick enough to justify placement in an ICU.

Vital signs monitoring is a prime means by which a patient is evaluated for adequacy of perfusion and oxygenation of the blood, and tracking their level and regulation is thus of great importance to the clinician. In particular, gross alterations of individual vital signs variables, such as heart rate (bradycardia and tachycardia) and blood pressure (hypotension and hypertension) and oxygen saturation (peripheral desaturation), are easily detected by the human eye examining a bedside monitor. Alterations of individual vital signs variables are themselves consequent upon many inter-related pathophysiological factors. Some patterns have abruptness of their onset and sharp, deep decrease or increase of the heart rate usually make them identifiable. However, there are many circumstances where no one vital sign variable that is monitored is markedly abnormal, yet the patient does experience an adverse event, such as an ischemic myocardial event. Likewise, there are many circumstances where patterns of alteration of vital signs emerge slowly, almost imperceptibly, owing to the extensive ability of the organ systems in the body to mount various physiologic compensatory changes to maintain the vital signs values within their normal ranges until at last the body's compensatory reserves have been exhausted. Accordingly, a serious shortcoming in the existing and conventional technologies is that they are unable to reliably detect emergence of an ischemic myocardial event based on monitoring and analyzing vital signs so as to detect an abnormality. (In contrast, embodiments of the disclosure solve this shortcoming in conventional technologies for detecting likely future occurrence of myocardial ischemia using techniques that are unknown in the industry, as described herein.)

The patterns of interrelationships among heart rate (HR), systolic blood pressure (SBP), and peripheral partial oxygen saturation (SpO2 or O2SAT) are complex and diverse. The rate of oxygen consumption by the heart muscle (myocardium) itself is, in turn, related to the intensity of work that the body demands of the heart. A close 'surrogate' measure of myocardial energy expenditure is the rate-pressure-product or RPP, defined as the heart rate multiplied by the systolic blood pressure. Hemodynamics reflected in these measurements' approximately co-synchronous values can be viewed as a type of nonlinear dynamic system. In order to characterize and predict the behavior of a complex nonlinear dynamic system, nonlinear dynamic theory is essential. Such theory aims to model the system's different aspects mathematically, yet many simplifications are necessary for a model to be feasible in practice, in near real-time. If the simplifications are reasonable ones, the model may be of considerable use, not only as an embodiment of the system represented and classification of the state that it is presently in, but also for its predictive capabilities regarding probabilities of alternative future states or events that may arise.

Accordingly, one type of nonlinear dynamic theory that can be applied to situations where gradually changing relationships are followed by abrupt changes in behavior is called catastrophe theory. Catastrophe theory is a special sub-field within the broader domain of nonlinear dynamic systems theory. It was introduced by mathematician Rene Thom. Thom criticized classical mathematics (the basis of many conventional technologies for determining likelihood of future myocardial ischemia occurrence) for its inability to predict discontinuous processes. He developed methods of determining how slow changes may produce sudden (hence, 'catastrophic') changes in the effects. Catastrophe theory provides mathematically continuous characterizations of discontinuous system behaviors.

A "catastrophe" therefore is a discontinuous change in the behavior, or structure, of a nonlinear dynamic system that occurs as one or a plurality of system parameters is varied. In many dynamic pathophysiological systems, it is possible to see a smooth response under conditions of normal physiologic homeostasis versus a discontinuous response to changes when physiologic compensatory mechanisms have become abnormal or when physiologic reserves have become depleted.

Figure 6:
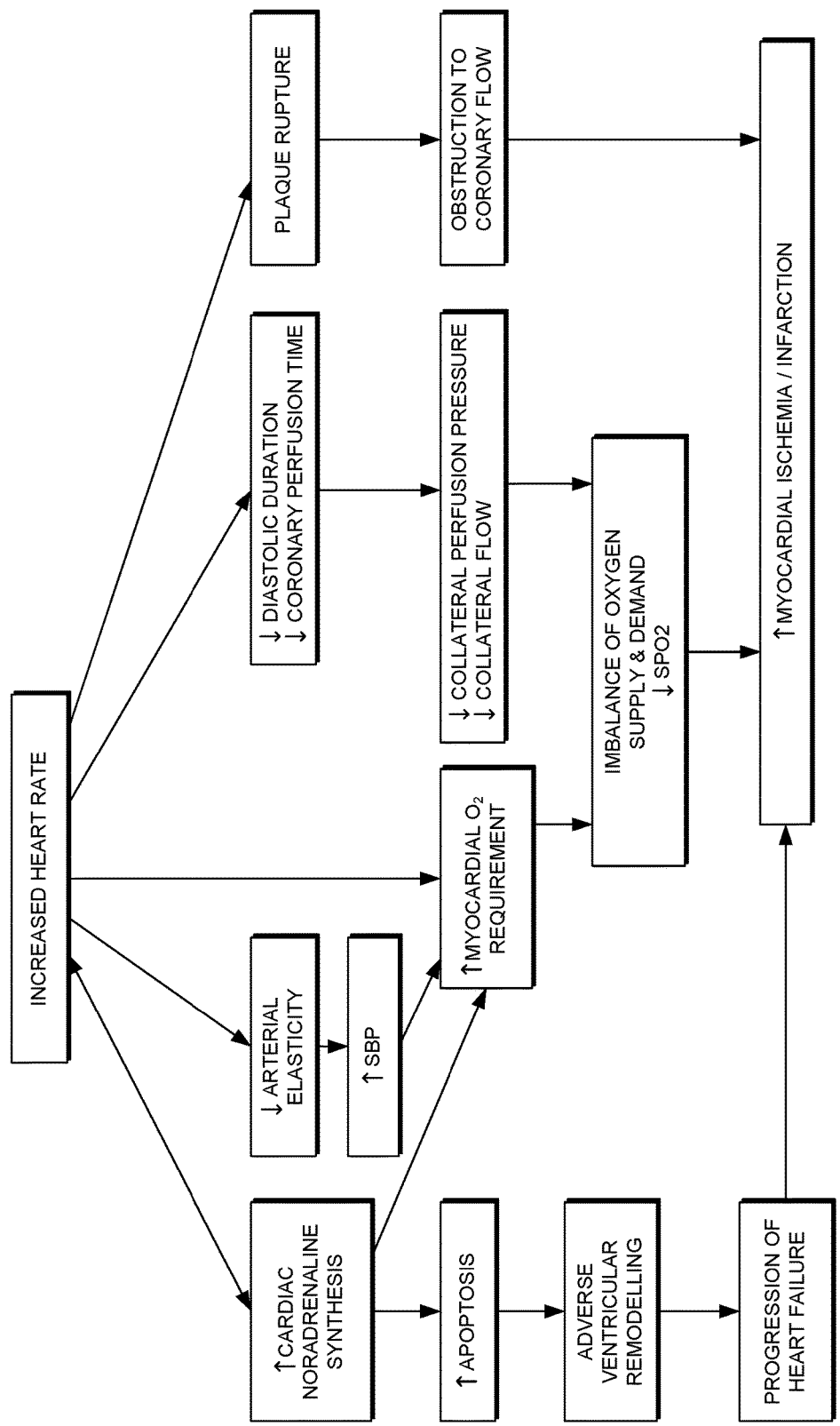
FIG. 6 depicts major interrelationships between physiologic processes that account for the normal linear and abnormal, myocardial ischemia-related nonlinear or catastrophe phenomena, in accordance with an embodiment of the disclosure.

Referring now to the drawings in general, and initially to FIG. 6 in particular, a block diagram is provided depicting major interrelationships between physiologic processes that account for the normal linear and abnormal, myocardial ischemia-related nonlinear or catastrophe phenomena, which are relevant to embodiments described herein. Referring now to FIG. 1A, an aspect of an operating environment 100 is provided suitable for practicing an embodiment of this disclosure. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus for readability, we show and reference items in the singular (while fully contemplating, where applicable, the plural).

As shown in FIG. 1, example operating environment 100 provides an aspect of a computerized system for compiling and/or running aspects of the an embodiment including predicting likelihood of myocardial ischemia for a patient within a future time interval. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, ambulatory clinic EHR systems, psychiatry/neurology EHR systems, and may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors, for example. Although FIG. 1A depicts an exemplary EHR system 160, it is contemplated that an embodiment relies on user/patient manager 140 and/or monitor 141 for storing and retrieving patient record information such as information acquired from monitor 141.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients for which the likelihood(s) of future occurrence of myocardial ischemia are determined according to the embodiments presented herein. Embodiments of interface 142 also facilitates accessing and receiving information from a user or health care provider about a specific patient or population of patients including patient history; health care resource data; physiological variables (e.g., vital signs) measurements, time series, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

An embodiment of patient manager 140 takes the form of a user interface and application, which may be embodied as a software application operating on one or more mobile computing devices, tablets, smartphones, front-end terminals in communication with back-end computing systems, laptops, or other computing devices. In an embodiment, manager 140 includes a Web-based application or set of applications usable to manage user services provided by an embodiment of the invention. For example, in an embodiment, manager 140 facilitates processing, interpreting, accessing, storing, retrieving, and communicating information acquired from monitor 141, EHR 160, or storage 121, including candidate diagnoses or conditions determined by embodiments of the invention as described herein. In an embodiment, manager 140 sends a notification (such as an alarm or other indication) directly to user/clinician interface 142 through network 175. In an embodiment, manager 140 sends a maintenance indication to provider clinician interface 142. In one embodiment of manager 140, an interface component may be used to facilitate access by a user (including a clinician/caregiver or patient) to functions or information on monitor 141, such as operational settings or parameters, user identification, user data stored on monitor 141, and diagnostic services or firmware updates for monitor 141, for example.

As shown in example environment 100, in one embodiment, manager 140 is communicatively coupled to monitor 141 and to network 175. In an embodiment, patient monitor 141 communicates via network 175 to computer 120 and/or provider clinician interface 142.

In an embodiment of monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, and which may be acquired periodically, continuously, as needed, or as they become available, and may be represented as one or more time series of measured variables. In one embodiment, monitor 141 comprises sensors for obtaining (and in some instances pre-processing or interpreting) non-invasive recording of vital signs, which may be obtained continuously, periodically, or at irregular intervals. For example, in an embodiments monitor 141 comprises a patient monitoring system such as Sotera ViSi®, Finapres® NOVA™, or Covidien ZephyrLIFE™. In some embodiments, monitor 141 comprises patient bedside monitor, such used in hospital. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from human measurements, human observations, or automatically determined by sensors in proximity to the patient. For example, in one embodiment, a nurse periodically measures a patients' blood pressure and enters the measurement and/or observations via manager 140 or interface 142. In another example, a nurse or caregiver enters one or more progress notes for an in-patient via manager 140 or interface 142. Similarly, values for vital signs variables may be entered via manager 140 or interface 142.

Examples of physiological variables monitored by monitor 141 can include vital signs variables, such as heart rate (bradycardia and tachycardia) and blood pressure (hypotension and hypertension) and oxygen saturation (peripheral desaturation), as described herein. Additionally, in some embodiments physiological variables monitored by monitor 141 may include, by way of example and not limitation, central venous pressure, other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making In an embodiment, a monitor such as 141 comprises a sensor probe, such as an EEG probe, and a communication link that periodically transmits identification information and probe data to patient manager 140, so that the time series of monitored values is stored on patient manager 140, enabling the patient manager to form a raw binary alarm indication and/or a physiological variable decision statistic. In an embodiment, patient monitor 140 collects raw sensor information, such as optical sensor 184, and performs signal processing, such as velocity measurement, forming a physiological variable decision statistic, cumulative summing, trending, wavelet processing, thresholding, computational processing of decision statistics, logical processing of decision statistics, pre-processing or signal condition, etc., part or all of which may be performed on monitor 141, manager 140, interface 142, and/or computer system 120.

An embodiment of monitor 141 stores user-derived data locally or communicates data over network 175 to be stored remotely. In an embodiment, manager 140 is wirelessly communicatively coupled to monitor 141. Manager 140 may also be embodied as a software application or app operating on a user's mobile device. In an embodiment, manager 140 and monitor 141 are functional components of the same device, such as a device comprising a sensor and a user interface. In an embodiment, manager 140 is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on monitor 141 or manager 140 for performing signal conditioning of the measured patient variable(s). In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, model variables indexing service 122 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126. Predictive models service 124 in general is responsible for providing multi-variable models for predicting near-term occurrence of ischemic myocardial events, such as the linear and cusp catastrophe models described in connection to method 200 of FIG. 2.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services. In an embodiment, computation services 126 and predictive models service 124 include the services or routines, which may be embodied as one or more software agents or routines such as the example embodiments of computer program routines illustratively provided in FIGS. 7A-7B. In one embodiment, computation services 126 comprises the R-System cusp package for cusp-catastrophe modeling and model fitting, which is invoked in the example computer program routines shown in FIGS. 7A-7B.

In some embodiments, stack 125 includes file system or cloud-services 128. Some embodiments of component 128 may comprise an Apache Hadoop and Hbase framework, or similar frameworks operable for providing a distributed file system, and which in some embodiments facilitate provide access to cloud-based services such as those provided by Cerner Healthe Intent®. Additionally, some embodiments of file system or cloud-services 128 or stack 125 may comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
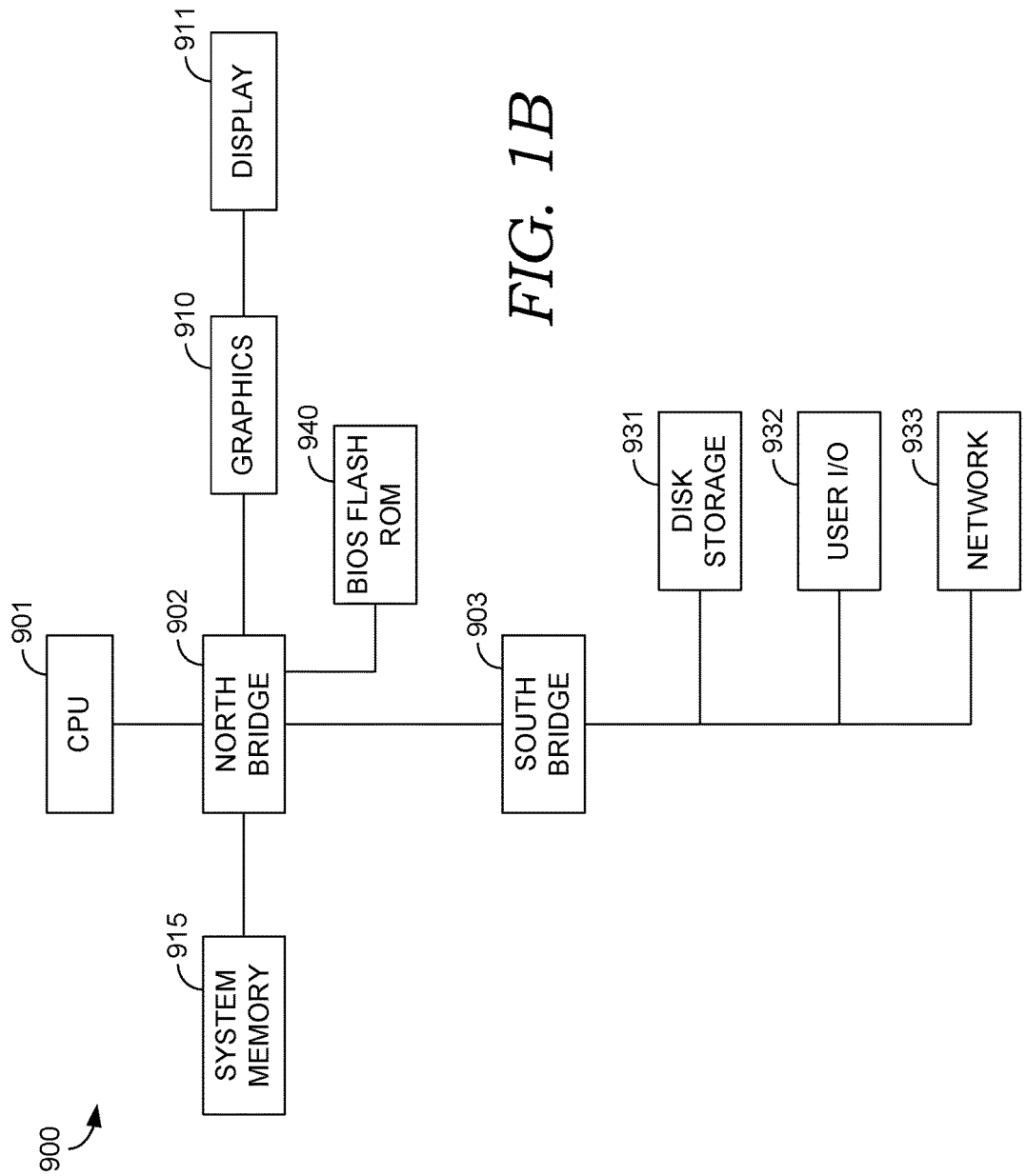

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
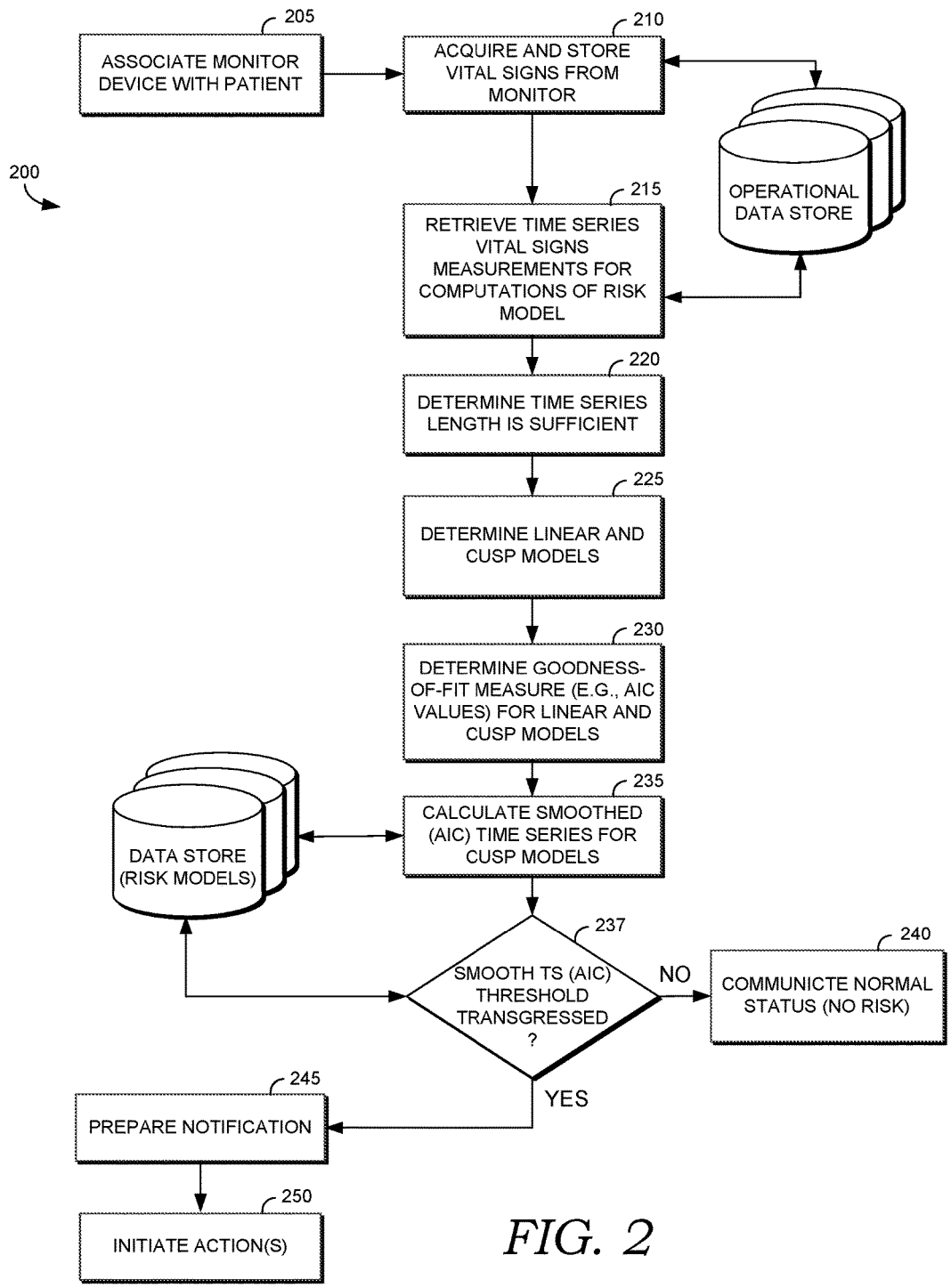
FIG. 2 depicts a flow diagram of a method for predicting an occurrence of a ischemic myocardial event for a human patient within a future time interval, in accordance with an embodiment of the disclosure.

Turning now to FIG. 2, one example embodiment of a method for predicting an occurrence of a ischemic myocardial event for a human patient within a future time interval is provided, and referred to generally as method 200. In particular, example method 200 utilizes catastrophe-theoretic approach for determining the probability of an ischemic myocardial event. As described previously, a catastrophe may be understood as a discontinuous change in the behavior, or structure, of a nonlinear dynamic system that occurs as one or a plurality of system parameters is varied. In some embodiments, aspects of method 200 may be carried out using the example computer program routine depicted in FIGS. 7A and 7B.

With reference to FIG. 2 and method 200, generally, in catastrophe theory, the phenomenon under study is assumed to be governed by a potential function, V. Stable states of the system may be regarded as minima of the function V. If the potential function has multiple minima, then more than one stable state may be accessible to the system at a particular time. Changing the control parameters may alter the form of the governing potential function so as to change the positions, relative heights, or total number of local minima. Thus, the observed state of a system may change in a discontinuous way as the controls are changed. The observed discontinuous changes in state are called catastrophes. A central proposition of catastrophe theory is the classification theorem, which states that, given a maximum of four control parameters which may themselves be composite variables comprised of a plurality of other variables, all discontinuous changes of events in a nonlinear system can be modeled by one of seven elementary topological types, each with a unique shape and set of mathematical properties. One of these includes cusp catastrophe.

Cusp Catastrophe. Turning briefly to FIGS. 3A-E, examples of cusp-type catastrophes are depicted. In particular, FIGS. 3A-3E show a plot of a curved surface with a pleat, called the system behavior surface, M, above a planar surface, C, over which two control factors vary. Mathematically, a cusp catastrophe is associated with a potential function of the form $V(x; a, b) = \frac{1}{4} x^4 + \frac{1}{2} ax^e + bx$, where a and b are the control factors and x is the variable whose behavior is plotted on the behavior surface. The topological feature of the behavior surface represents the graph of all points where the first derivative of this function is equal to zero.

This catastrophe surface arises from consideration of extrema (particularly minima) of the potential. The first derivative of the cusp function is $\partial V(x; a, b)/\partial x = x^3 + ax + b$. The glimpse at the mathematical foundation of the theory given here is meant to demonstrate that the graphic representations of the cusp catastrophe in the present invention are not arbitrary configurations or ex post facto constructions. In particular, when plotting the behavior surface, most combinations of control factors a and b result in a unique solution for setting the derivative equal to zero. These unique solutions are points of stable equilibrium or the most likely mode of behavior for the particular combination of control factors. The set of these points represents the areas that define the stable, non-pleated part of the behavior surface.

But for some combinations of control factors there are multiple stable equilibria, and multiple modes of behavior. Thus, in the middle of the plot the M surface folds upon itself and overlaps, and makes a continuous pleated surface with a 'cusp' where the pleat is. The cusp or pleated part represents unstable equilibria and points on this surface region are generally inaccessible to the system. Variation in the control factors in the area of the pleat will shift the behavioral variable between the upper and lower stable surfaces on M. Even though the changes in the control variables are continuous and smooth, as reflected by the smooth continuity of the pleated surface, small changes in their relative levels cause sudden, discontinuous changes in the system's behavior. The discontinuous jump between stable surfaces is a catastrophe. Both smooth and catastrophic change can occur with a cusp catastrophe model.

Catastrophe Flags.

There are five inter-related qualitative features or 'flags' that can be associated with a catastrophe surface. These five catastrophe flags are effective for determining the presence or absence of a catastrophe-type nonlinearity behavior of the system from which the data represented on the surface originate.

Modality.

This means that the system has two or more distinct states that may exist. In other words, the potential describing the system has more than one local minimum for some range of the external control parameters. The cusp catastrophe becomes bimodal when the control parameters lie within the cusp-shaped region.

Inaccessibility.

This means that the system has an equilibrium state which is unstable. Such equilibria are unstable because infinitesimal perturbations exist which decrease the value of the potential function V. Whenever the potential V has more than one local minimum, it must have at least one unstable equilibrium. The two sheets over the cusp-shaped region, representing the locally stable minima, are separated by the pleated region, representing an unstable local maximum.

Sudden Jumps.

A small change in the value(s) of one or more control parameters may result in a large change (sudden jump) in the value of the state variable as the system jumps from one local minimum to another. The transition from the neighborhood of one local minimum to another represents a large change in the value of the behavior state variable, which often occurs on a fairly rapid time scale. A sudden jump in the value of the state variable occurs as the system state jumps from a region on one side of the cusp catastrophe manifold to the other.

Divergence.

Usually a small perturbation in the values of the control parameters will lead to only a small change in the initial and final values of the state variables. However, in the neighborhood of the cusp, small changes in the control parameter's initial values may lead to large changes in the state variable's subsequent values. The instability of processes against perturbation of the control parameter trajectory is called divergence.

Hysteresis.

This occurs whenever a process is not strictly reversible. That is, the jump from one local minimum 'A' to a different local minimum 'B' does not occur over the same point in control parameter space as the jump transiting in the other direction, from local minimum 'B' to local minimum 'A'. For the cusp catastrophe, hysteresis occurs when the jump from one sheet to another does not occur for the same values of the control parameters as the reciprocal jump.

Any one or more of these five catastrophe flags suggest or indicate the presence of a catastrophe-type discontinuity.

Catastrophe theoretic models describe hemodynamic abnormalities that are prodromic to ischemic myocardial events as an abrupt response to changing physiological compensation. Because of its three-dimensionality and topological features, the cusp catastrophe model provides a qualitatively consistent characterization of vital signs variables' interrelationships. The smooth fold curve or pleat connecting the two surfaces implies that the variables regulating the change between patterns act in a continuous fashion even though the switch from one pattern to the other is discontinuous. It is this qualitative characteristic of vital signs time series patterns that immediately precede the onset of an ischemic myocardial event that results in such time series' being well-fit by a catastrophe model. Whenever continuously changing control parameters have an abruptly changing effect, the process may be well represented by a catastrophe model.

The fundamental theorems of catastrophe theory do not require an explicit knowledge of the potential V; they may apply generically to all smooth (mathematically differentiable) potential functions. Provided there is a good reason to believe that the dynamics of a system (vital signs and hemodynamics variables, as in the context of embodiments described herein) is such that it tends to minimize some smooth function V(x; a, b) that depends on two parameters, as here, then a cusp-type catastrophe is likely. The validity of this approach is independent of our knowledge of the manner in which V is minimized A main feature of the modeling process(es) in embodiments of this disclosure in this regard is the assumption of the existence of such a potential. The important point is not whether a given equilibrium is stable or not, but whether it persists over moderate intervals of time as physiologic compensations, or therapeutic and preventive maneuvers, or other factors in the system change.

Accordingly and in light of the foregoing, method 200 begins at step 205, wherein a monitor device, such as monitor 141, is associated with the patient. In one embodiment, step 205 comprises physically attaching a patient to the device and/or associating a monitor-device identifier (ID) with the patient, such that patient data acquired via the device is associated with the patient. In one embodiment, a patient account or patient EHR is associated with the monitor.

At step 210, vital sign (or physiological) variables are acquired for the patient. In one embodiment, these variables comprise HR, SBP, and SpO2 measurements, which may be acquired using the monitor device. Embodiments of step 210 may acquire the vital signs measurements continuously, periodically, or at non-regular intervals. The measured variables may be stored in a data store, such as storage 121, and may be stored in an EHR associated with the patient. In some embodiments, the date/time information for the measurements is stored with the measured variable values such that a time series may be determined.

At step 215, the historical measurements of the patient's vital signs are retrieved and a time series is determined. The time series may be constructed by appending the most recent vital signs measurements to the historical measurements, using the associated date-time information. In some embodiments, the historical measurements comprise measurements obtained within a recent timeframe such as the previous several hours, last 6 hours, last 12 hours, or previous 24 hours. In such embodiments, only historical measurements from within this recent timeframe are retrieved and used for the constructing time series.

At step 220, the time series may be evaluated to determine whether it is of sufficient length. In an embodiment, where the time series is determined to be greater than a pre-determined length, method 200 proceeds to step 225. But if the time series is not long enough, then method 200 returns to step 210, where additional vital signs measurements may be acquired. In one embodiment, the pre-determined length comprises 100 samples, and in another embodiment, the pre-determined length comprises 1000 samples. In one embodiment, step 220 further comprises determining that the measurements are of a sufficiently minimum frequency, such as measurements obtain on the order of every few seconds or several times per minute. Further still, in some embodiments, step 220 (or of method 200, prior to step 225), may standardize and center each of the variables' time series values.

At step 225, linear and cusp models are determined. Embodiments of step 225 may determine the linear and cusp models based on a boxcar of the time series comprising N recent samples. In one embodiment comprises approximately 100 samples, and in another embodiment, N comprises approximately 500 to 600 samples, which may provide greater accuracy. An example embodiment of step 225 is illustratively provided in the computer program routine shown in FIGS. 7A and 7B. This example embodiment uses the cusp package (computation services 126, in FIG. 1A) of the R-system.

At step 230, a goodness-of-fit measure may be determined for the linear and cusp models. In one embodiment, step 230 comprises determining Akailke Information Criterion (AIC) values for the linear and cusp models. AIC represents a measure of the relative quality of statistical models for a given set of data. Thus, for a collection of models for the data, AIC estimates the quality of each model, relative to each of the other models. Hence, AIC may be used as a means for model selection. In another embodiment of step 230, a Bayesian Information Criterion (BIC), or other suitable criterion may be determined. In further embodiments, Cobb's maximum likelihood method and the maximum likelihood method for linear modeling may be used.

At step 235, the time series may be smoothed for the cusp model(s). Embodiments of step 235 may perform a de-noise operation on the AIC (or BIC) time series, which may be implemented using a low-pass filter. In this way, the likelihood of false alarms may be reduced. However, the smoothing applied at step 235 is not so great that detection of the ischemic event is delayed until it is impending. One embodiment of step 235 comprises using a Hanning filter (Hanning window), which may be configured to approximately five to seven points. In on embodiment, Exponentially-Weighted Moving Average (EWMA) is used to determine the smoothed time series of the AIC values.

At step 237, it is determined whether the smoothed time series threshold is transgressed. Embodiments of step 237 may thus determine the classification or probability of future myocardial ischemia occurrence within the defined future time interval based on whether the smoothed cusp model AIC threshold is transgressed or, alternately, based on whether a threshold for the ratio of linear-to-cusp model AIC values is exceeded. Where the threshold is transgressed, exceeded (or otherwise satisfied), method 200 proceeds to step 245; but where the threshold is not satisfied, then method 200 proceeds to step 240.

In embodiments of step 237, the threshold may be pre-determined and may be context-dependent. The threshold is determined empirically, in an embodiment, and may be set according to a table (or function) for a particular context, such as the patient condition, available resources for patient care, and/or the intensity of care. For example, in one embodiment, the threshold may be based on healthcare resources such as staffing or level of care already being received by the patient. Thus, where the patient is already receiving active care and monitoring, such as in a surgical ICU, a higher threshold may be used such that exceeding (or satisfying) the threshold could lead to paging (or notifying) the surgeon and may also lead to taking the patient back to the OR. But a lower threshold may be used where a patient is, say, in a labor and delivery unit (e.g. a birthing suite) following post-partum hemorrhage, and not presently receiving a high level of care.

At step 240, where the threshold is not exceeded or satisfied, method 200 may end, or may otherwise report that the patient is not at risk for a myocardial ischemia within a future time horizon. At step 245, where the threshold in step 237 has been satisfied and thus a significant risk for myocardial ischemia exists, a notification of the determined risk, such as described previously, may be generated. Some embodiments of step 245 may comprise storing the result of the determination in an electronic health record (EHR) associated with the patient, and further, may include providing the patient's EHR (or facilitating access to the EHR) in the notification. In some embodiments, step 245 may be part of step 250.

At step 250, based on the determined likelihood, a set of one or more actions may be initiated in response to determining significant risk of a myocardial ischemia event. For example, as described herein, a notification may be generated and emitted or otherwise communicated to a provider clinician(s) responsible for the care of the patient; a recommendation for modifying a care plan or treatment procedure associated with the patient may be generated and provided; computer code executed in a healthcare software program for treating the patient, may be modified, thereby transforming the program at runtime; healthcare resources may be scheduled or arranged; or other actions may be initiated in response to the determined risk. In some embodiments, the initiated actions may be based on the level of risk (i.e. the probability that a myocardial ischemia event will occur, such as a high or moderate likelihood), and/or how impending the event is likely to occur (e.g. how far into the future time interval, which may provide a sense of urgency). Some embodiments of the steps of method 200 may be carried out using the example computer program routine depicted in FIGS. 7A and 7B. Additionally, in some embodiments, method 200 may utilize Cobb's maximum likelihood method and the maximum likelihood method for linear modeling.

With reference to FIGS. 4A, 4B, 5A, 5B, and 6, and continuing reference to method 200 of FIG. 2 and FIGS. 3A-3E, examples are provided of an embodiment of the disclosure constructively reduced to practice. Here, computer system 120 running the Linux operating system (129) was utilized with the open-source statistical software package R, and the R module cusp (Computation services 126). In this example embodiment, an observational study of was performed using a consented, secondary-use-rights-granted data set. Illustrative series of vital signs (approximately co-synchronous HR, SBP, and SpO2 measurements) values were retrieved from a subset of persons having previous electrocardiogram (ECG) and laboratory-confirmed coronary artery disease (CAD) and at least one diagnosed acute myocardial infarction (AMI), whose de-identified, confidentiality-protected health records were stored and maintained in Cerner's Health Facts® data warehouse. The cohort selected was comprised of CAD patients for whom Health Facts® contained at least 1,000 serial vital signs values measured over a period of not less than 4 hours and at a rate of not less than one sample per 5 seconds. Positive cases in this cohort were patients who experienced an in-hospital infarction or re-infarction, ascertained by the presence of new ECG changes plus elevation of serum cardiac troponin I (cTnI) levels. Negative controls in this cohort were patients who did not experience an in-hospital infarction or re-infarction, ascertained by the absence of ECG changes and the absence of elevation of cardiac troponin I (cTnI) levels.

FIGS. 3B through 3E, respectively, show examples of positive cases wherein near-term future myocardial ischemic events were preceded by multivariable relationships that were better modeled by cusp catastrophe model than by a linear model.

Vital signs data may be visualized on a three-dimensional plot (e.g., FIG. 3B) comprised of two surfaces. On the two dimensions of the lower plane control surface C the asymmetry variable's value and the bifurcation variable's value can be plotted. The system's equilibria can be projected vertically to show the response variable on the upper, folded surface M. Above the cusp-shaped region on C lie the upper, lower, and pleat surfaces of the folded area of M. The response usually lies either on the upper surface or lower surface (that is, it is bimodal across the pleat or cusp) and it is least likely to lie in the interior of the pleat surface of M.

The two-dimensional control surface C allows the changing forces of bifurcation b (control parameter b) and physiological compensation a (control parameter a) to be plotted. At any time the equilibrium between these forces can be projected vertically (response) onto the surface of the upper folded surface M. The raised portion represents baseline heart rate, and the lower part represents transient bradycardia.

Figure 3B:
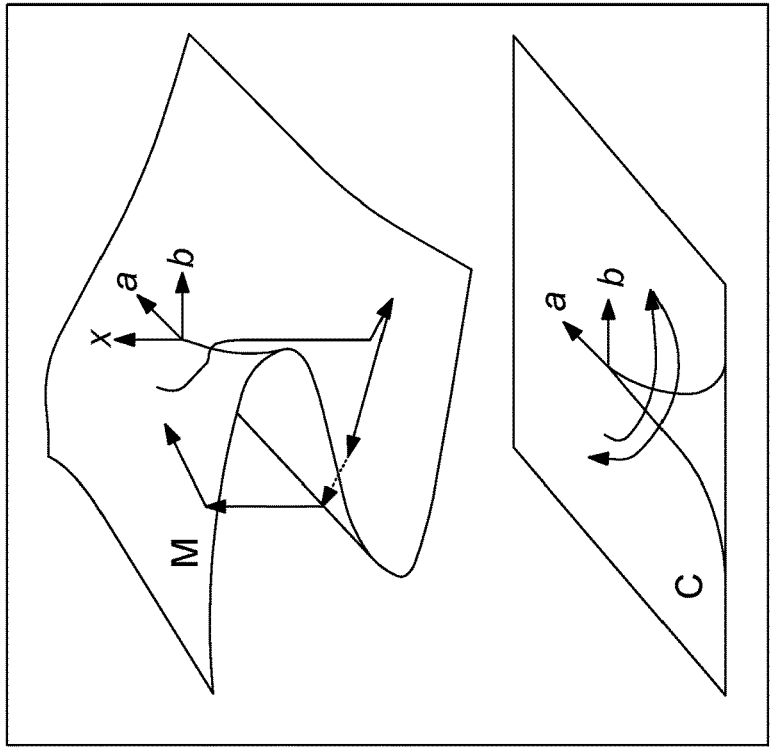
FIGS. 3A-3E each depict an illustrative example of a positive case wherein near-term future myocardial ischemic events were preceded by multivariable relationships that were better modeled by cusp catastrophe model than by a linear model, in accordance with an embodiment of the disclosure.
Figure 3A:
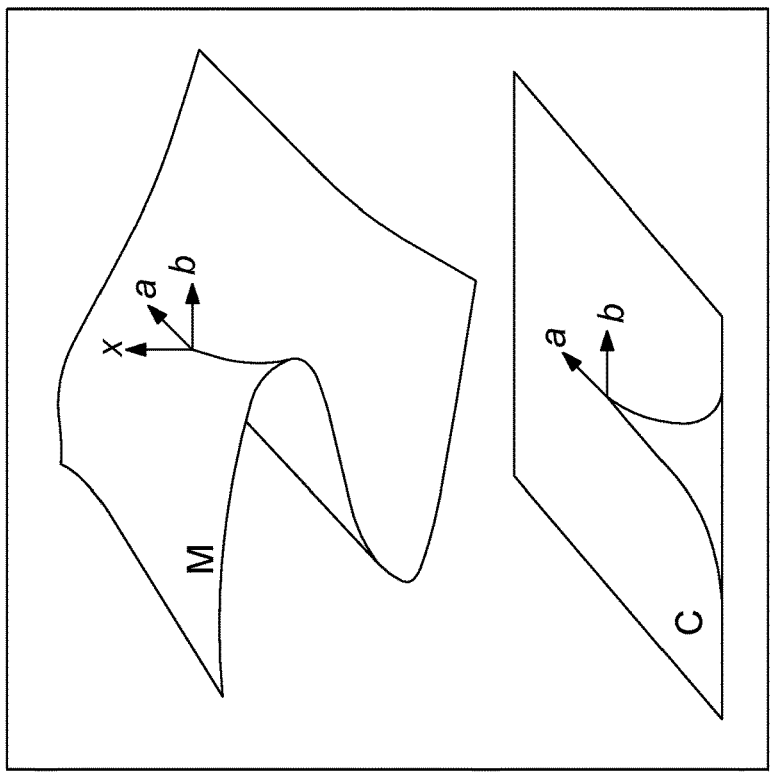
Figure 3D:
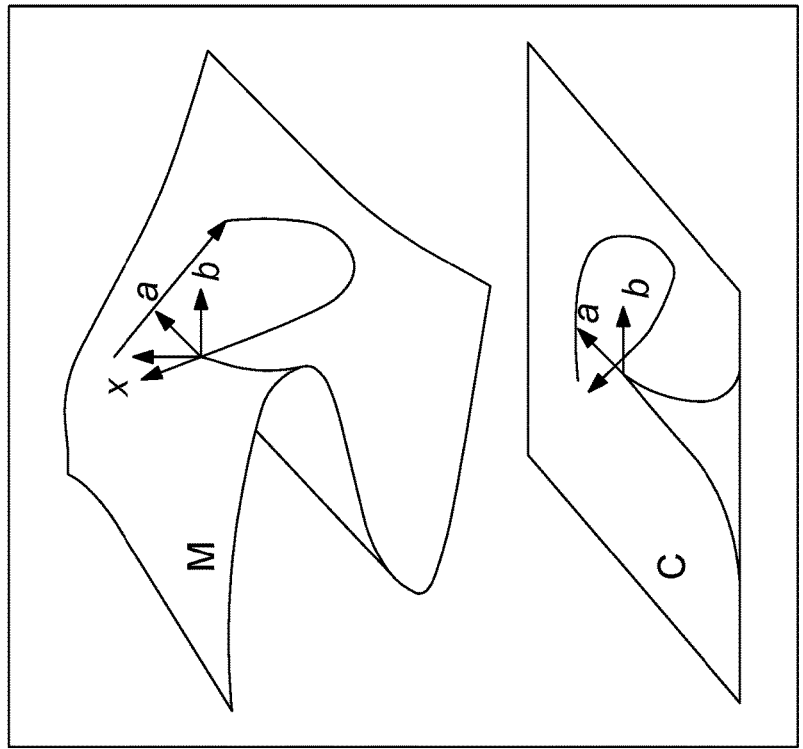
Figure 3C:
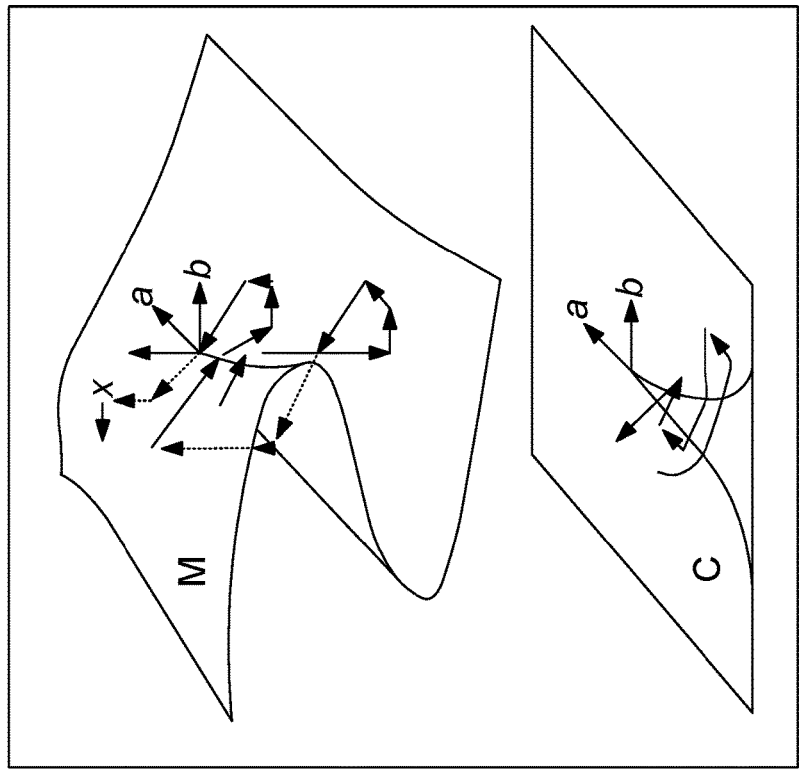

FIG. 3D shows an abnormal response surface approximately 1 hour prior to onset of extension of an existing AMI. A state of acute hypertension resulted in stimulation of systemic baroreceptors and an abrupt fall in heart rate. The magnitude of fall in the heart rate varies directly with the magnitude of the hypertension, a reflection of the abnormal impedance of arterial flow. The curved line on the control plane C shows the movement of the equilibrium point in this case, drawing the equilibrium point into and through the area beneath the folded surface of M. The response projected vertically onto the upper response surface M is indicated by the heavy line, carried onto the upper surface of the bimodal area, indicating that the baseline heart rate is normal. Eventually, as the equilibrium point on C moves out of the bifurcation set, the line projected on M reaches the folded edge of the upper surface on M and falls onto the lower folded surface, representing deceleration (bimodality and inaccessibility flags). This is the sudden discontinuity, or catastrophe, in response to the slowing changing forces plotted on C (sudden jump flag).

Figure 3E:
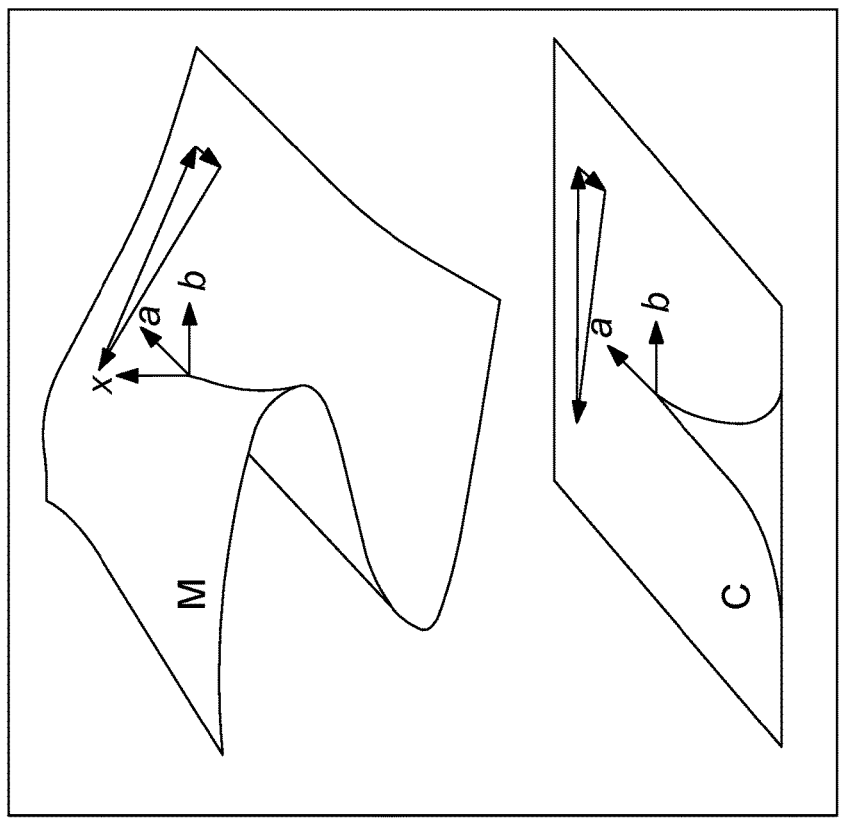

FIG. 3E shows a record of abnormal hemodynamics preceding ECG evidence of the onset of new AMI by approximately 30 min.

Figure 4A:
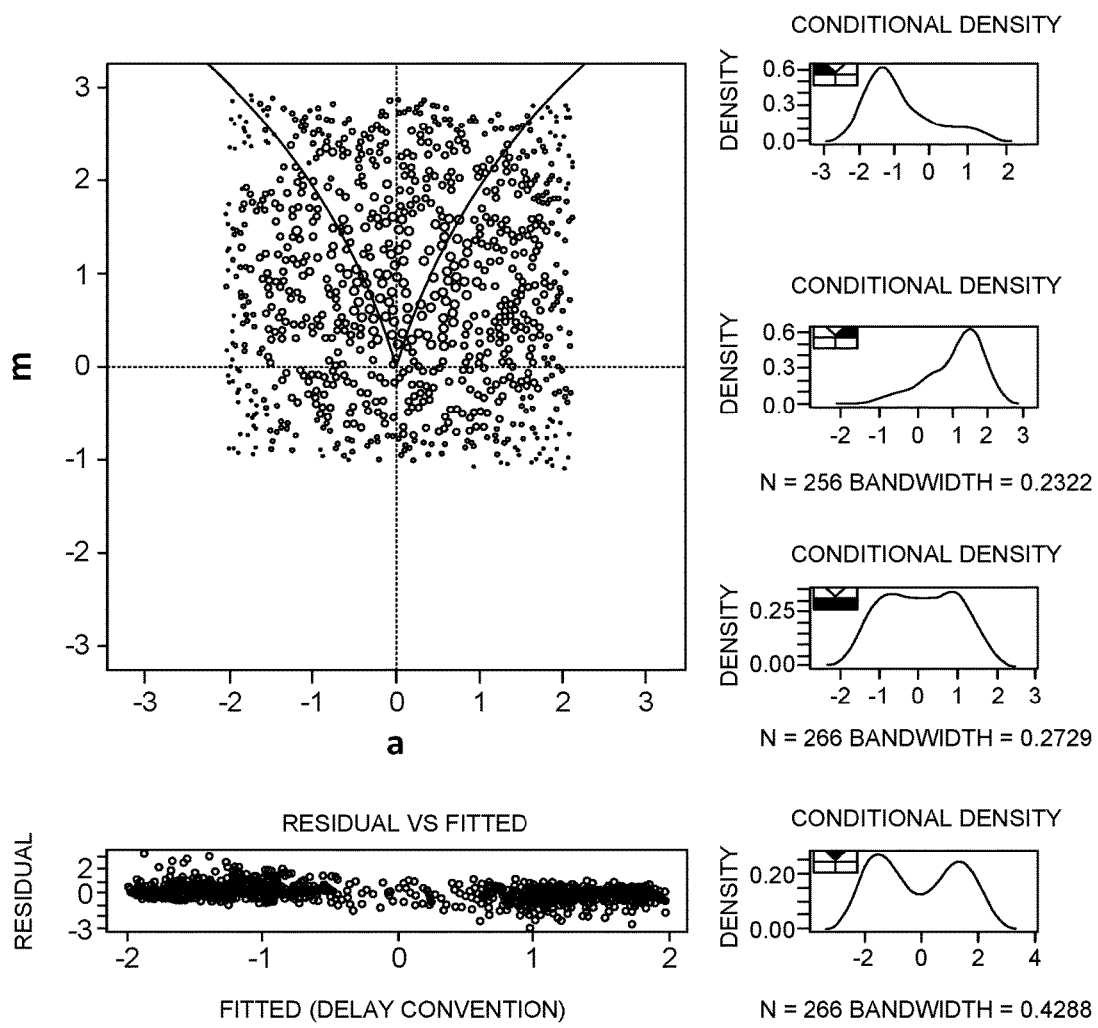
FIGS. 4A-4B depict an example time series segments' "linear:cusp" model AIC ratios and an associated exponentially-weighted moving average "ischemia alarm signal" determined from an AIC ratio time series, using an example embodiment that has been reduced to practice, for a patient who developed new onset of AMI while in-hospital.
Figure 4B:
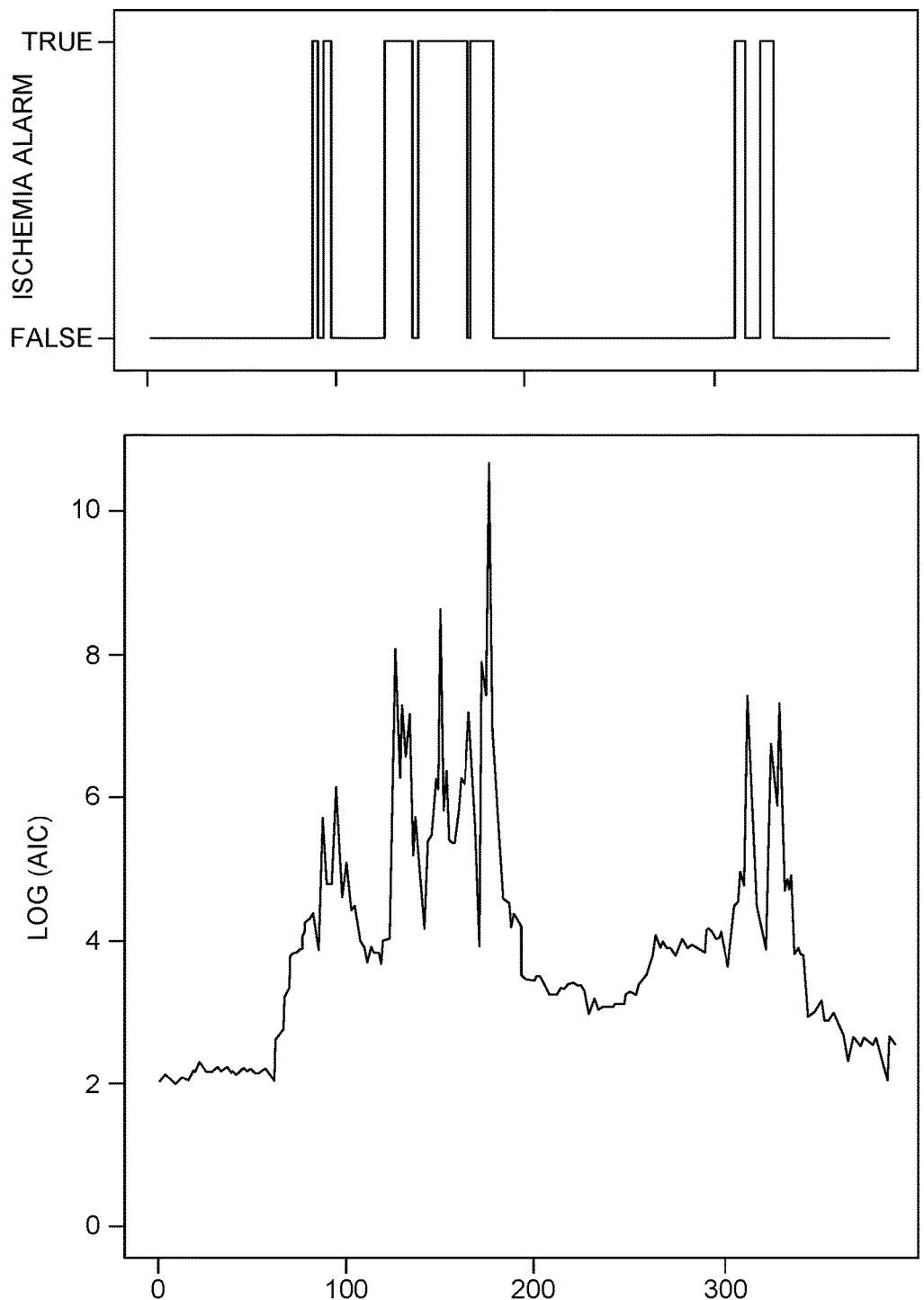

FIG. 4A-4B depict a plot of 400 consecutive 200-long time series segments' "linear:cusp" model AIC ratios and the associated exponentially-weighted moving average "ischemia alarm signal" determined from the AIC ratio time series, in a patient who developed new onset of AMI while in-hospital. In contrast, FIG. 5A-5B show a plot of 400 consecutive 200-long time series segments' "linear:cusp" model AIC ratios and the associated exponentially-weighted moving average "ischemia alarm signal" determined from the AIC ratio time series, in a patient who did not experience an ischemic myocardial event while in-hospital.

These figures demonstrate the how the application of embodiments generate significant advancements to decision support systems. By employing the particular techniques discussed herein, embodiments of the decision support system were able to accurately generate warning alarms for a patient who developed a new onset of AMI while in-hospital. For example, FIG. 4A-4B, are graphical representations of the decision support system's findings after employing the particular techniques described herein for a patient who suffered from an onset of AMI. FIG. 4A depicts a time series segments' "linear:cusp" model AIC ratios. FIG. 4B is the associated exponentially-weighted moving average "ischemia alarm signal" determined from an AIC ratio time series. Referring to FIG. 4B, the lower graph depicts a log(AIC), which is represented by the y-axis, and time-series segments, which is represented by the x-axis. Note that where the spikes occur in the lower graph of FIG. 4B, embodiments signaled an ischemia alarm (represented by the graph on the top). Accordingly, for the patient who in fact suffered from a new onset of AMI, using the systems and processes described herein provided an accurate determination.

Figure 5A:
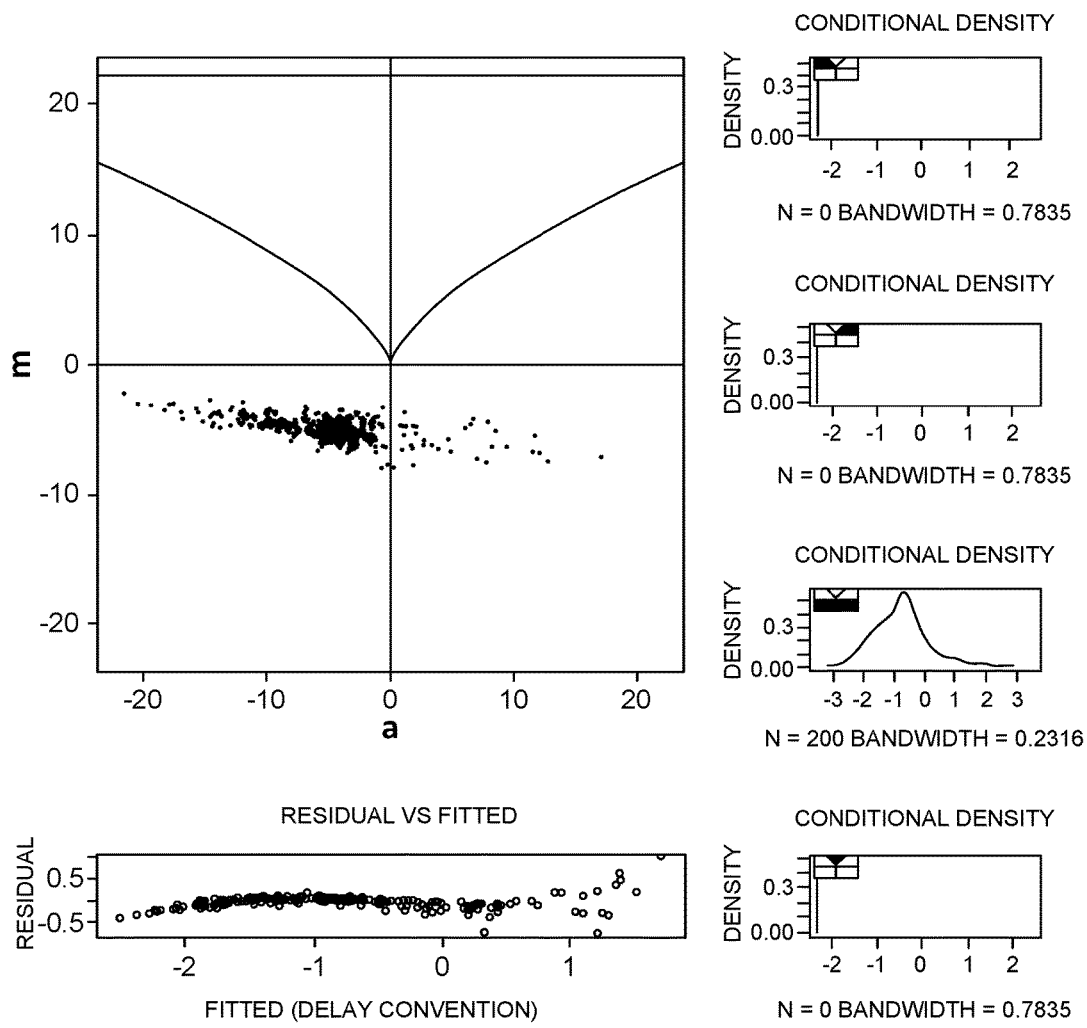
FIGS. 5A-5B depict an example time series segments' "linear:cusp" model AIC ratios and an associated exponentially-weighted moving average "ischemia alarm signal" determined from an AIC ratio time series, using an example embodiment that has been reduced to practice, for a patient who did not experience an ischemic myocardial event while in-hospital.
Figure 5B:
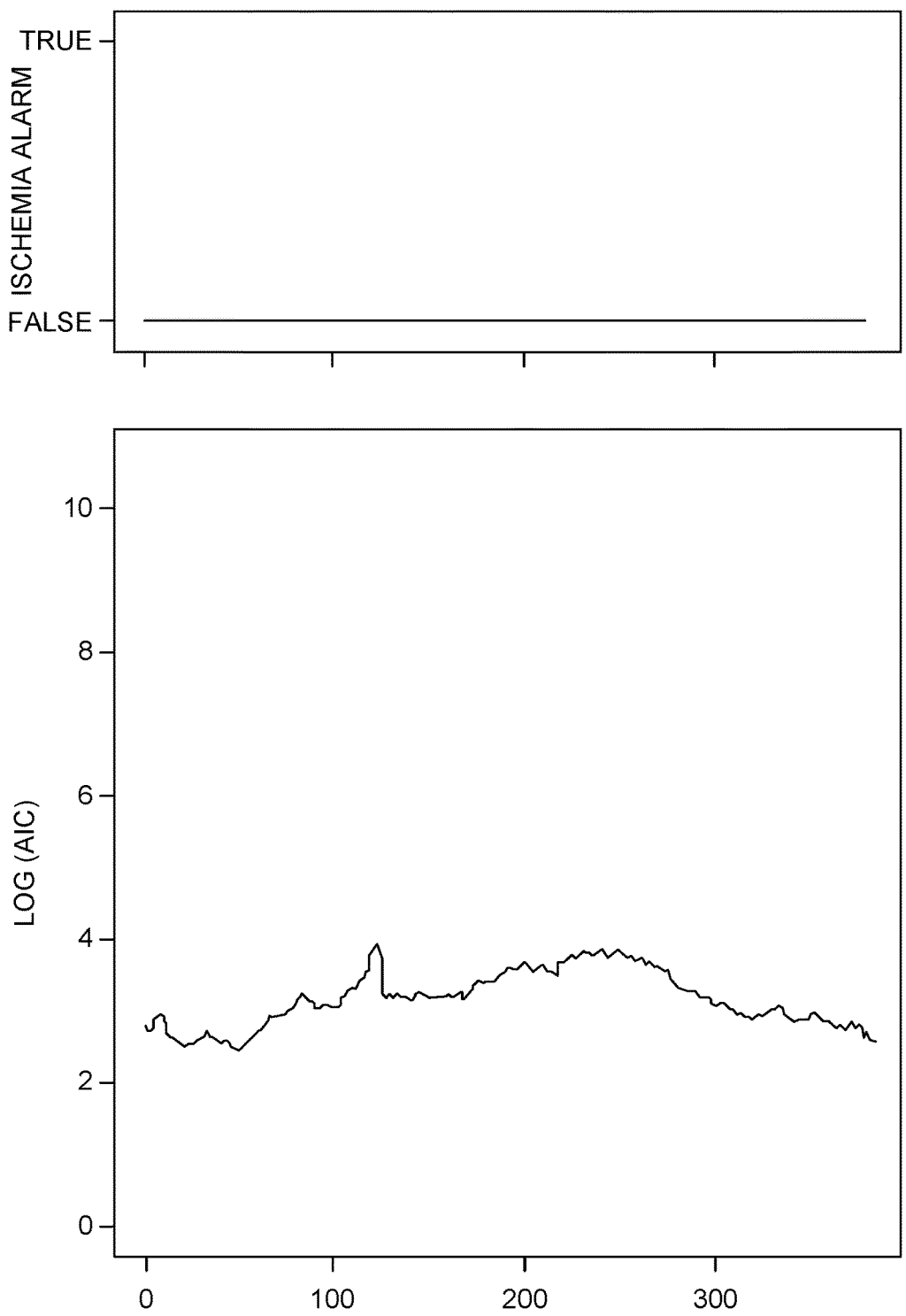

Similarly, FIG. 5A-5B are graphical representations of the decision support's findings after employing the particular techniques described herein for a patient who did not suffer from an onset of AMI. FIG. 5A depicts an example time series segments' "linear:cusp" model AIC ratios. FIG. 5B is an associated exponentially-weighted moving average "ischemia alarm signal" determined from an AIC ratio time series it. Referring to FIG. 5B, the lower graph depicts a log(AIC), which is represented by the y-axis, and time-series segments, which is represented by the x-axis. Note that embodiments (correctly) did not signal an ischemia alarm for a patient that did not suffer from an onset of AMI. As such, FIGS. 4-5 depict how employing the technical solutions described herein solves a need of greater accuracy and reliability that is unmet in current technologies. That is, the technical solutions of the present application overcome the drawbacks associated with conventional methods.

In some embodiments, computer-readable media has computer-executable instructions embodied thereon that, when executed, provide a decision support system for anticipating myocardial ischemia. The method comprises acquiring, using one or more patient monitors, a plurality of measurements of vital signs for the patient, the vital sign measurements acquired over a timespan. The acquisition of the vital signs data is performed with a frequency not less than once per minute, preferably at least once per 15 seconds, or more preferably at least once per 5 seconds. The vital signs acquired may include a patient's heart rate (HR), systolic blood pressure (SBP), and peripheral oxygen saturation (SpO2) at intervals of time. In the event a variable may be missing, intermittent sensor error or artifact or signal drop-out or other causes of missingness of individual instances of HR, SBP, and SpO2 measurements affect not more than 10% of the values in a time series segment to be processed.

Continuing with this embodiment, a vital signs time series may then constructed from the acquired measurements. The time series of each vital signs variable is optionally standardized (scaled to have standard deviation=1.0 and centered to have mean=0.0) prior to fitting. It is contemplated that the transformed, standardized SpO2 measurements may be inverted, so that positive extremal scaled, centered values are abnormal and negative values correspond to SpO2 measurements in the normal range. A computer processor then determines a linear model and cusp catastrophe model based on the vital signs time series, and calculates a goodness-of-fit measure for the linear model and cusp model. A likelihood of the patient experiencing a myocardial ischemia occurrence over a future timeframe may then be determined by determining that the cusp model transgresses a first threshold or exceeds a second threshold for the ration of linear-to-cusp model. The first and second threshold may be context-dependent and pre-determined. It is contemplated that the determined likelihood of the patient experiencing a myocardial ischemia comprises one of a numerical probability from zero to one hundred or a category-label of high, moderate, or low. Based on the determined likelihood, the decision support system may initiate a response action to avoid patient mortality.

In alternative embodiments, a system forecasts emergent myocardial ischemic events in a patient having coronary artery disease. The system may comprise one or more sensors that are configured to acquire physiological data from a patient. The system may further comprise one or more processors and memory with stored computer-useable instructions that, when executed by the one or more processors, implement a method that comprises the step of using the one or more sensors to acquire vital signs values. A time series from the acquired vital signs values may then be determined. A linear model and cusp catastrophe-theoretic model may be generated based on the determined time series. The cusp catastrophe modeling may be performed on subsets of the measurements time series, such that each subset is comprised of a plurality of approximately co-synchronous measurements, preferably not less than 100 time points and not more than 1,000 time points.

Continuing with this embodiment, the method may further include quantitatively evaluating the linear model or a cusp catastrophe-theoretic model to determine which model better accounts for the variation in the time series, and selecting that model thereby determining a performance criterion time series. The fitting of the time series data, in some embodiments, is performed by Cobb's maximum likelihood method for cusp-catastrophe modeling and by a maximum likelihood method for linear modeling. It is contemplated that qualitatively evaluating comprises a comparative goodness-of-fit of cusp versus linear models that may be represented by the 'linear-to-cusp model information criterion ratio' of the respective models' Akaike Information Criterion (AIC) values or Bayesian Information Criterion (BIC) values or similar goodness-of-fit measures as are known to those in the art.

Continuing with this embodiment, the criterion time series may then be determined using a threshold. Based on satisfying a threshold, an elevated risk of an ischemic myocardial event for the patient may be determined. Based on the determined risk, a response action to treat the patient or mitigate the determined risk may be initiated. It is contemplated that the alarm signal predicting a near-term future ischemic event may be determined when ln(linear:cusp AIC)>5.0 or the linear:cusp AIC ratio >150 for a significant duration, preferably a period of 90 sec or longer.

In alternative embodiments, a cusp catastrophe model potential function may be comprised of one or more vital signs variables or composite variables derived from raw vital signs variables. In addition, the cusp catastrophe model potential function may be the rate-pressure-product (RPP), while the cusp catastrophe model asymmetry function may be a multivariable function, preferably a function of heart rate (HR) and systolic blood pressure (SBP). Meanwhile, the cusp catastrophe model bifurcation function may be a multivariable function, preferably a function of heart rate (HR) and peripheral oxygen saturation (SpO2).

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. Computer-readable media having computer-executable instructions embodied thereon that when executed by one or more processors, provide a method for anticipating myocardial ischemia, the method comprising:
   acquiring, using one or more patient monitors, a plurality of measurements of vital signs for the a patient, the vital sign measurements acquired over a timespan;
   constructing, via the one or more computer processors, a vital signs time series from the acquired measurements;
   determining, via a the one or more computer processors, a linear model and cusp catastrophe model based on the vital signs time series;
   calculating, via the one or more computer processors, a goodness-of-fit measure for the linear model and cusp model;
   determining, via the one or more computer processors, a likelihood of the patient experiencing a myocardial ischemia occurrence over a future timeframe by determining that the cusp model transgresses a first threshold or exceeds a second threshold for a ratio of linear-to-cusp model; and
   based on the determined likelihood, initiating a response action to avoid patient mortality.

2. The computer-readable media of claim 1, wherein the cusp model is based on an asymmetry function, the asymmetry function comprising a heart rate (HR) and a systolic blood pressure (SBP).

3. The computer-readable media of claim 1, wherein the cusp model is based on a potential function comprising a rate-pressure-product (RPP).

4. The computer-readable media of claim 1, wherein the cusp model is based on a model bifurcation function, the model bifurcation function comprising a heart rate (HR) and a peripheral oxygen saturation ($S_pO_2$).

5. The computer-readable media of claim 1, wherein calculating the goodness-of-fit measure comprises determining Akaike Information Criterion (AIC) values for the linear and cusp models.

6. The computer-readable media of claim 5, further comprising determining a smoothed AIC time series for the cusp model.

7. The computer-readable media of claim 6, wherein the smoothed AIC time series is determined using an Exponentially-Weighted Moving Average (EWMA) operation.

8. The computer-readable media of claim 1, wherein the initiated response action comprises one or more of: automatically generating and communicating an electronic notification to a provider clinician(s) responsible for a care of the patient; generating and providing a recommendation for modifying a care plan or treatment procedure associated with the patient; modifying computer code executed in a healthcare software program for treating the patient; or scheduling healthcare resources for the patient.

9. The computer-readable media of claim 8, wherein the modified computer code executed in the healthcare software program comprises a software healthcare agent associated with the care plan for the patient.

10. The computer-readable media of claim 8, wherein the notification includes information indicating the determined likelihood of the patient experiencing a myocardial ischemia.

11. The computer-readable media of claim 1, wherein the vital signs time series comprises at least one hundred date-time measurements.

12. A system for forecasting emergent myocardial ischemic events in a patient having coronary artery disease, comprising:
   one or more sensors configured to acquire physiological data from the patient;
   one or more processors;
   memory storing computer-useable instructions that, when executed by the one or more processors, implement a method comprising:
   acquiring, using the one or more sensors, vital signs values;
   determining a time series from the acquired vital signs values;
   generating a linear model and a cusp catastrophe-theoretic model based on the determined time series;
   quantitatively evaluating the linear model and the cusp catastrophe-theoretic model to determine which model better accounts for a variation in the time series;
   determining a performance criterion time series by selecting the model that better accounts for the variation in the time series;
   evaluating the performance criterion time series using a threshold;
   based on satisfying a threshold, determining an elevated risk of an ischemic myocardial event for the patient; and
   based on the determined risk, initiating a response action to treat the patient or mitigate the determined risk.

13. The system of claim 12, wherein in the vital signs values comprise values for heart rate (HR), systolic blood pressure (SBP), and peripheral oxygen saturation (SpO2) of the patient at intervals of time.

14. The system of claim 13, further comprising deriving a multiplicative rate-pressure-product (RPP) from the HR and SBP measurements.

15. The system of claim 14, wherein the determined time series further includes the RPP.

16. The system of claim 12, further comprising smoothing the performance criterion time series.

17. The system of claim 16, wherein the smoothing the time series is performed by an Exponentially-Weighted Moving Average (EWMA) operation.

18. The system of claim 12, wherein the performance criterion time series comprises a goodness-of-fit metrics time series, and further comprising determining a transgression of a reference range for the goodness-of-fit metrics time series, thereby determining a near-term risk of the ischemic myocardial event.

19. The system of claim 12, further comprising a data store configured for storing and logging indications of forecast ischemic events for the patient, and configured for use in preventing or mitigating a severity of subsequent myocardial ischemic events.

20. The system of claim 12, wherein cusp catastrophe modeling is performed on subsets of measurements time series, such that each subset comprises a plurality of approximately co-synchronous measurements not less than 100 time points and not more than 1,000 time points.

\* \* \* \* \*

UNITED STATES PATENT AND TRADEMARK OFFICE
CERTIFICATE OF CORRECTION

PATENT NO. : 10,390,765 B1
APPLICATION NO. : 15/395696
DATED : August 27, 2019
INVENTOR(S) : Douglas S. McNair It is certified that error appears in the above-identified patent and that said Letters Patent is hereby corrected as shown below:

In the Drawings

FIG. 2, reference numeral 240: Please remove "COMMUNICTE" and replace with --COMMUNICATE--.

In the Specification

Column 07, Line 67: Please remove "the an" and replace with --an--.

Column 10, Line 40: Please remove "making" and replace with --making.--.

Column 13, Line 50: Please remove "axe+bx," and replace with --ax2+bx,--.

Column 16, Line 36: Please remove "Akailke" and replace with --Akaike--.

In the Claims

Column 21, Line 35: Please remove "the a" and replace with --the--.

Column 21, Line 63: Please remove "($S_pO_2$)." and replace with --($SpO_2$).--.

Column 22, Line 59: Please remove "(SpO2)" and replace with --($SpO_2$)--.

Column 31, Line 39: Please remove "a the" and replace with --the--.

Signed and Sealed this
Twenty-ninth Day of October, 2019

Andrei Iancu
*Director of the United States Patent and Trademark Office*